United States Patent [19]

Yamamoto et al.

[11] Patent Number: 5,698,748
[45] Date of Patent: Dec. 16, 1997

[54] PROCESS OF PRODUCING HYDROXYALKANAL

[75] Inventors: Hiroshi Yamamoto; Hisakazu Shindou, both of Suita; Tadahiro Yoneda, Ibaragi, all of Japan

[73] Assignee: Nippon Shokubai Co., Ltd., Osaka, Japan

[21] Appl. No.: 560,716

[22] Filed: Nov. 20, 1995

[30] Foreign Application Priority Data

Nov. 22, 1994 [JP] Japan ................... 6-288308

[51] Int. Cl.$^6$ ................... C07C 29/141
[52] U.S. Cl. ................... 568/862; 568/458
[58] Field of Search ................... 568/458, 862

[56] References Cited

U.S. PATENT DOCUMENTS

| | | | |
|---|---|---|---|
| 2,434,110 | 1/1948 | Hatch et al. | 260/602 |
| 3,536,763 | 10/1970 | Eleuterio et al. | 260/602 |
| 4,146,574 | 3/1979 | Onoda et al. | 423/299 |
| 5,015,789 | 5/1991 | Arntz et al. | 568/862 |
| 5,093,537 | 3/1992 | Unruh et al. | 568/862 |
| 5,171,898 | 12/1992 | Arntz et al. | 568/862 |
| 5,276,201 | 1/1994 | Haas et al. | 568/491 |
| 5,284,979 | 2/1994 | Haas et al. | 568/491 |

*Primary Examiner*—C. Warren Ivy
*Assistant Examiner*—Sreeni Padmanabhan
*Attorney, Agent, or Firm*—Kubovcik & Kubovcik

[57] ABSTRACT

A process of producing hydroxyalkanal comprises a step of hydrating a raw material, namely, an unsaturated aldehyde, in an aqueous solution in the presence of a lead-carrying heterogeneous acid catalyst promoting the hydration reaction. According to the above method, the lead-carrying heterogeneous acid catalyst curbs the consecutive reaction of the reaction product, namely, hydroxyalkanal. Thus, hydroxyalkanal can be produced with high selectivity at high yield out of a high-concentration unsaturated aldehyde solution. Moreover, the catalyst can be used repetitively for a considerable period of continuous use in a stable manner, thereby further improving the yield of hydroxyalkanal.

12 Claims, No Drawings

PROCESS OF PRODUCING HYDROXYALKANAL

FIELD OF THE INVENTION

The present invention relates to a process of producing hydroxyalkanal by hydrating an unsaturated aldehyde in an aqueous solution in the presence of a catalyst.

BACKGROUND OF THE INVENTION

In conventional processes, an unsaturated aldehyde, namely, acrolein, is hydrated in an aqueous solution in the presence of a catalyst to obtain hydroxyalkanal, namely, 3-hydroxypropanal(3-hydroxypropionaldehyde), which will be explained in the following paragraphs.

U.S. Pat. No. 2,434,110 discloses a process, in which a mineral acid, such as a sulfuric acid, is used as a homogeneous acid catalyst for the above reaction step. However, 3-hydroxypropanal retains low selectivity in this process, and thus is not produced efficiently. In addition, neither is 3-hydroxypropanal readily separated from the homogeneous catalyst, nor can the catalyst be re-used easily.

To eliminate such a drawback, processes for improving the selectivity of 3-hydroxypropanal are proposed in the following publications. U.S. Pat. No. 3,536,763 discloses a process in which an acid ion exchange resin is used as an heterogeneous acid catalyst for the above reaction step. U.S. Pat. No. 5,015,789 and U.S. Pat. No. 5,171,898 disclose processes, in which an ion exchange resin containing a phosphonate group, an amino group, or an aminophosphate group is used as a heterogeneous acid catalyst for the above reaction step. U.S. Pat. No. 5,093,537 discloses a process in which alumina bonding zeolite is used as a heterogeneous acid catalyst for the above reaction step. U.S. Pat. No. 5,276,201 discloses a process in which $TiO_2$ carrying a phosphoric acid is used as a heterogeneous acid catalyst for the above reaction step. Also, U.S. Pat. No. 5,284,979 discloses a process in which the above reaction is performed using a buffer solution containing a carboxylic acid and a tertiary amine in the presence of an acid catalyst.

If a resulting solution of the raw material, acrolein, has low concentration (i.e., lower than 20 percent by weight), 3-hydroxypropanal retains satisfactory selectivity, thereby making it possible to obtain 3-hydroxypropanal at high selectivity by the above processes.

More precisely, U.S. Pat. No. 5,171,898 discloses a reaction step in which ion exchange resins each respectively carrying Na, Mg, and Al are used as the heterogeneous acid catalyst and the concentration of the raw material, namely, acrolein, is set to about 17 percent by weight. In this case, the selectivity of 3-hydroxypropanal as a result of the hydration is as high as 81–85%.

However, the inventors of the present invention found that when an industrially advantageous high-density acrolein solution (i.e., 20 or more percent by weight) is used for the reaction in each of the above processes, a reaction product, 3-hydroxypropanal, triggers an active consecutive reaction (side reaction) because it has an aldehyde group. In other words, the above processes have a drawback that the selectivity from acrolein to 3-hydroxypropanal, and hence the selectivity of 3-hydroxypropanal is reduced.

In addition, the heterogeneous acid catalyst used in the above conventional processes has poor durability, and is not used repetitively for the hydration reaction. Therefore, neither is the catalyst used repetitively, nor does increasing the concentration of acrolein solution improve the yield of 3-hydroxypropanal by the above processes, indicating that these processes are not satisfactory in terms of industrial use.

SUMMARY OF THE INVENTION

It is therefore an object of the present invention to provide a process capable of (1) solving the problems caused by the conventional processes, (2) using a catalyst repetitively, and (3) producing hydroxyalkanal at high selectivity out of an industrially advantageous high-concentration unsaturated aldehyde solution.

To fulfil the above object, the inventors of the present invention performed experiments of processes for producing hydroxyalkanal by hydrating an unsaturated aldehyde in an aqueous solution in the presence of a catalyst, and found that the selectivity from an unsaturated aldehyde to hydroxyalkanal and the yield of hydroxyalkanal were improved when a lead-carrying heterogeneous acid catalyst was used for the hydration reaction.

Also, it was determined that the heterogeneous acid catalyst rendered excellent durability and could be used repetitively. More specifically, the gist of the present invention is to use a lead-carrying heterogenous acid catalyst, and the effect is that (1) the heterogeneous acid catalyst can be used repetitively in promoting the hydration reaction for a considerably long period of continuous use in a stable manner, and (2) hydroxyalkanal is produced with high selectively and at a high yield out of an industrially advantageous high-concentration unsaturated aldehyde solution.

In other words, to solve the above problems, a process of producing hydroxyalkanal in accordance with the present invention comprising a step of hydrating a raw material, namely, an unsaturated aldehyde, in an aqueous solution in the presence of a catalyst promoting the hydration reaction is characterized in that the catalyst is a lead-carrying heterogeneous acid catalyst.

The present invention is explained more in detail in the following paragraphs.

An unsaturated aldehyde (2-alkenal) used as a raw material in the present invention is not especially limited. However, an industrially preferable unsaturated aldehyde is expressed by Formula (I) below, where R represents either a hydrogen atom or a hydrocarbon group having up to five carbons. The hydrocarbon group is a methyl group, an ethyl group, a propyl group, a butyl group, or an amyl group.

(I)

Examples of the above unsaturated aldehyde are: acrolein, methacrolein, 2-formyl-1-butene, 2-formyl-1-pentene, 2-formyl-1-hexene, 2-formyl-1-heptene, and the like. Of these examples, a preferable unsaturated aldehyde is acrolein.

According to the process in accordance with the present invention, either 2-hydroxyalkanal or 3-hydroxyalkanal is selectively obtained from these examples. More precisely, in case of acrolein whose substitutional group represented by R in Formula (I) is a hydrogen atom, 3-hydroxyalkanal, namely, 3-hydroxypropanal (i.e., 3-hydroxypropionaldehyde) is selectively obtained.

In case of an unsaturated aldehyde whose substitutional group represented by R in Formula (I) is a hydrocarbon group, 2-hydroxyalkanal is selectively obtained. Note that 3-hydroxypropanal, obtained when acrolein is used as the unsaturated aldehyde, is an industrially important raw material of 1,3-propanediol.

The concentration of an unsaturated aldehyde solution (hereinafter referred to as the concentration) is, although it depends on solubility of the unsaturated aldehyde in water, reaction temperature, etc., preferably in a range between 5 percent by weight and saturation, more preferably in a range between 5 percent by weight and 50 percent by weight, further preferably in a range between 20 percent by weight and 50 percent by weight, and most preferably in a range between 25 percent by weight and 40 percent by weight. A concentration lower than 5 percent by weight is not preferable because the yield of hydroxyalkanal is reduced. The concentration exceeding saturation is not preferable either because an undissolved unsaturated aldehyde triggers a polymerization reaction or the like and thus reduces the selectivity to hydroxyalkanal.

A preferable catalyst used in the present invention is a lead-carrying heterogeneous acid catalyst, examples of which are: an ion exchange resin, a (meta)acrylic acid-(meta)acrylamide copolymer, and solid non-organic materials, such as zeolite. Of these examples, preferable catalysts are an ion exchange resin and a (meta)acrylic acid-(meta)acrylamide copolymer.

One or more than one kind of the heterogeneous acid catalysts is used. An amount of the heterogeneous acid catalyst with respect to the unsaturated aldehyde is not especially limited, and can be determined depending on the kinds of the unsaturated aldehyde and heterogeneous acid catalyst. A process of producing the heterogeneous acid catalyst is not especially limited either.

Although it depends on the kinds of the heterogeneous acid catalyst, the amount of lead carried by the heterogeneous acid catalyst is preferably in a range between 0.001 percent by weight and 10 percent by weight, more preferably in a range between 0.01 percent by weight and 5 percent by weight, and most preferably in a range between 0.01 percent by weight and 1 percent by weight. A lead-carrying amount less than 0.001 percent by weight is not preferable because it is not sufficient to realize the effect of the lead-carrying heterogeneous acid catalyst. A lead-carrying amount exceeding 10 percent by weight is not preferable either because the yield of hydroxyalkanal is reduced.

Note the terminology "lead-carrying" referred to herein does not specify a particular form, in other words, either a salt or chelate and either an adsorption type or inclusion type will do. Also, either lead ions or lead metal will do. Examples of lead ions are an oxide, a halide, a sulfide, and the like.

A process of converting a heterogeneous acid catalyst into a lead-carrying heterogeneous acid catalyst is not especially limited, and it can be performed in any known manner. For example, when the heterogeneous acid catalyst is an ion exchange resin, the ion exchange resin is soaked in a solution of a predetermined amount of a compound, such as a lead nitrate and a lead acetate, and stirred under predetermined conditions to perform a cation exchange. Subsequently, the ion exchange resin is collected by filtration or the like and rinsed with water.

The reason why a lead-carrying heterogenous acid catalyst produces an excellent function and effect in the reaction for producing hydroxyalkanal from an unsaturated aldehyde is not apparent. However, the lead-carrying heterogeneous acid catalyst is assumed to curb the consecutive reaction (side reaction) of the reaction product, hydroxyalkanal. The reason why the lead-carrying heterogeneous acid catalyst renders excellent durability is not apparent either. However, the lead-carrying heterogeneous acid catalyst is assumed to bond with lead tightly and thus not release lead easily.

A reaction temperature is not especially limited, but a preferable range is between 50° C. and 250° C. In case that acrolein is used as the unsaturated aldehyde, a preferable range is between 50° C. and 140° C. A reaction temperature below 50° C. is not economically preferable because reaction speed is decreased and the hydration reaction takes a long time. A reaction temperature exceeding 250° C. is not preferable either because there occurs a side reaction, such as polymerization of the unsaturated aldehyde, thereby reducing the yield of hydroxyalkanal.

The present invention can be performed in a batch, semi-batch, or continuous manner, but in any case, a closed vessel is preferred for the reaction step. A reaction pressure inside the closed vessel is not especially limited, but a preferable range is between 1 kg/cm$^2$ and 20 kg/cm$^2$.

In case that a reaction takes place below a boiling point of the unsaturated aldehyde, it is preferable to apply a reaction pressure in a range between 1 kg/cm$^2$ and 5 kg/cm$^2$ to the reaction vessel by taking the vaporization pressure of the unsaturated aldehyde and other ingredients into consideration. The above reaction pressure is applied, for example, by filling an inert gas ($N_2$ gas, He gas, etc.) into the reaction vessel.

The higher the reaction pressure, the more the unsaturated aldehyde dissolves in water and the higher the yield of hydroxyalkanal becomes. On the other hand, the anti-pressure structure of a reaction vessel must be reinforced, which increases the size of the vessel undesirably. Thus, when setting a reaction pressure, these factors must be taken into consideration.

When the reaction ends, the object product, a hydroxyalkanal solution, can be readily obtained by a simple separation process, such as filtration and distillation. Further, the hydroxyalkanal can be readily separated from the solution if so desired.

In case of 3-hydroxyalkanal of the hydroxyalkanals, it may exist in the form of a hemiacetal and an acetal in the solution, but this does not cause any trouble in the above separating process because the hemiacetal and acetal can be easily converted into 3-hydroxyalkanal.

Likewise, hydroxyalkanal, in the presence of alcohol, may exist in the form of a hemiacetal and an acetal of the corresponding alcohol, but this does not cause any trouble in the above separating process because they can be easily converted into a hydroxyalkanal.

Note that the collected water, catalyst, unreacted unsaturated aldehyde can be used repetitively for the hydration reaction.

According to the above process, when the catalyst is the lead-carrying heterogeneous acid catalyst, it can be repetitively used, and the consecutive reaction (side reaction) of the reaction product, namely, hydroxyalkanal, is curbed. Thus, hydroxyalkanal can be produced with high selectively and at a high yield out of a high-concentration unsaturated aldehyde solution.

In other words, the above process is suitable for producing hydroxyalkanal because it can use the catalyst repetitively for a considerable period of continuous use in a stable manner and trigger a reaction of an industrially advantageous high-concentration unsaturated aldehyde solution, and thus improve the yield of hydroxyalkanal.

Hereinafter, the present invention is illustrated by the following examples of preferred embodiments in comparison with comparative examples not according to the invention. However, the present invention is not limited to the undermentioned examples. Note that an invert ratio of the unsaturated aldehyde and the selectivity of the resulting hydroxyalkanal are defined as follows:

(1) An invert ratio of unsaturated aldehyde(%)=(the mole number of consumed unsaturated aldehyde/the mole number of supplied unsaturated aldehyde)×100

(2) Selectivity of hydroxyalkanal(%)=(the mole number of unsaturated aldehyde converted into hydroxyalkanal/the mole number of consumed unsaturated aldehyde)×100

(3) Selectivity of dimerized hydroxyalkanal=(the mole number of unsaturated aldehyde converted into dimerized hydroxyalkanal/the mole number of consumed unsaturated aldehyde)×100.

The amounts of the unsaturated aldehyde, hydroxyalkanal, and dimerized hydroxyalkanal are measured in any known manner, and gas chromatography (GC), one of known methods, is used in the present invention.

Other objects and advantages of the present invention will become apparent from the following detailed description taken in conjunction with the appended claims.

DESCRIPTION OF THE EMBODIMENT

[First Example]

A predetermined amount of water is poured into a reaction vessel equipped with a thermometer, a stirring instrument, and the like, and a predetermined amount of an unsaturated aldehyde, namely, acrolein, is also poured into the reaction vessel, so that the concentration of the resulting solution is 17 percent by weight. Next, a predetermined amount of a lead-carrying ion exchange resin (i.e., heterogeneous acid catalyst) serving as a catalyst promoting the hydration reaction is added to the solution. "Duolite" of Rohm & Haas Co. is used as the ion exchange resin, and an amount of lead of the lead-carrying ion exchange resin is 0.4 percent by weight. Note that the ion exchange resin includes an aminophosphate group as an acid group.

The above reaction solution is subjected to reaction for five hours with stirring at 60° C. to hydrate the acrolein. When the reaction ends, the resulting reaction solution is filtered, and analyzed in a predetermined manner, the results of which are set forth below.

(1) invert ratio of acrolein: 71%

(2) selectivity of 3-hydroxypropanal: 81%

(3) selectivity of dimerized 3-hydroxypropanal: 10%

(4) selectivity of hydroxyalkanal: 91% (total of (3) and (4))

The collected catalyst had excellent durability and can be used repetitively for the hydration reaction.

There is produced a solution containing 8.1 percent by weight of 3-hydroxypropanal and 1.3 percent by weight of dimerized 3-hydroxypropanal obtained as the result of the above hydration reaction. A known raney nickel catalyst is added to the resulting solution to hydrogenate the 3-hydroxypropanal and dimerized 3-hydroxypropanal. Reaction conditions are: a hydrogen pressure of 100 kg/cm$^2$, a reaction temperature of 60° C., and a reaction time of six hours.

When the reaction ends, the resulting solution is analyzed and it is acknowledged that there is produced 1,3-propanediol in an amount equal to the total of 3-hydroxypropanal and dimerized 3-hydroxypropanal. In other words, 1,3-propanediol is produced quantitatively. This indicates that almost all the dimerized 3-hydroxypropanal is converted into 1,3-propanediol by a known hydrogenation process.

[Second Example]

An analysis is conducted in the same manner as the first example except that the reaction time is cut to two hours, the results of which are set forth below.

(1) invert ratio of acrolein: 50%

(2) selectivity of 3-hydroxypropanal: 70%

(3) selectivity of dimerized 3-hydroxypropanal: 11%

(4) selectivity of hydroxyalkanal: 81% (total of (3) and (4))

The collected catalyst had excellent durability and can be used repetitively for the hydration reaction.

[Third Example]

A predetermined amount of water is poured into a reaction vessel equipped with a thermometer, a stirring instrument, and the like, and a predetermined amount of an unsaturated aldehyde, namely, acrolein, is also poured into the reaction vessel, so that the concentration of the resulting solution is 17 percent by weight. Next, a predetermined amount of a catalyst, namely, a lead-carrying acrylic acid-N,N-dimethylaminopropylacrylamide copolymer (i.e., heterogeneous acid catalyst) is added to the solution. The acrylic acid-N,N-dimethylaminopropylacrylamide copolymer contains 5 percent by mole of N,N-dimethylaminopropylacrylamide. The amount of lead of the above lead-carrying copolymer is kept equal to or lower than a predetermined level, namely, not more than 5 percent by weight. Note that the above copolymer contains a carboxyl group as an acid group.

The above reaction solution is subjected to reaction for four hours with stirring at 80° C. to hydrate the acrolein. When the reaction ends, the resulting reaction solution is filtered, and analyzed in a predetermined manner, the results of which are set forth below.

(1) invert ratio of acrolein: 54%

(2) selectivity of 3-hydroxypropanal: 61%

(3) selectivity of dimerized 3-hydroxypropanal: 14%

(4) selectivity of hydroxyalkanal: 75% (total of (3) and (4))

The collected catalyst had excellent durability and can be used repetitively for the hydration reaction.

[Fourth Example]

An analysis is conducted in the same manner as the third example except that the concentration of the unsaturated aldehyde, or namely, acrolein, is increased to 28 percent by weight from 17% by weight and the reaction time is cut to three hours, the results of which are set forth below.

(1) invert ratio of acrolein: 33%

(2) selectivity of 3-hydroxypropanal: 61%

(3) selectivity of dimerized 3-hydroxypropanal: 22%

(4) selectivity of hydroxyalkanal: 83% (total of (3) and (4))

The collected catalyst had excellent durability and can be used repetitively for the hydration reaction.

[First Comparative Example]

An analysis is performed in the same manner as the first example except that (1) an ion exchange resin that does not carry lead is used instead of the lead-carrying ion exchange resin, and (2) the reaction time is cut to three hours, the results of which are set forth below.

(1) invert ratio of acrolein: 56%

(2) selectivity of 3-hydroxypropanal: 64%

(3) selectivity of dimerized 3-hydroxypropanal: 6%

(4) selectivity of hydroxyalkanal: 70% (total of (3) and (4))

The collected catalyst had poor durability and can not be used repetitively for the hydration reaction.

[Second Comparative Example]

An analysis is performed in the same manner as the third example except that (1) acrylic acid-N,N-dimethylaminopropylacrylamid copolymer that does not carry lead is used instead of the lead-carrying acrylic acid-N,N-dimethylaminopropylacrylamide copolymer, and (2) the reaction time is cut to three hours, the results of which are set forth below.

(1) invert ratio of acrolein: 41%

(2) selectivity of 3-hydroxypropanal: 61%

(3) selectivity of dimerized 3-hydroxypropanal: 6%

(4) selectivity of hydroxyalkanal: 67% (total of (3) and (4))

The collected catalyst had poor durability and can not be used repetitively for the hydration reaction.

The above results reveal that, in the process of each of the examples in accordance with the embodiment of the present invention, using the lead-carrying ion exchange resin or acrylic acid-N,N-dimethylaminopropylacrylamide copolymer as a catalyst promoting the hydration reaction of the raw material, namely, unsaturated aldehyde, can curb the consecutive reaction of the reaction product, namely, 3-hydroxypropanal. Thus, 3-hydroxypropanal can be produced with high selectively at high yield out of a high-concentration acrolein solution.

In addition, the above catalysts have excellent durability and thus can be used repetitively for a considerable period of continuous use in a stable manner.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process of producing hydroxyalkanal comprising a step of producing hydroxyalkanal by hydrating an unsaturated aldehyde in an aqueous solution in the presence of a catalyst promoting a hydration reaction, said catalyst being a lead-carrying heterogeneous acid catalyst.

2. The process as defined in claim 1, wherein an amount of lead of said lead-carrying catalyst is in a range between 0.001 percent by weight and 10 percent by weight.

3. The process as defined in claim 1, wherein an amount of lead of said lead-carrying catalyst is in a range between 0.01 percent by weight and 1 percent by weight.

4. The process as defined in claim 1, wherein said unsaturated aldehyde is expressed by Formula (I) below, where R represents one of a hydrogen atom and a hydrocarbon group having up to five carbons

5. The process as defined in claim 1, wherein said unsaturated aldehyde is acrolein.

6. The process as defined in claim 1, wherein said catalyst is an ion exchange resin.

7. The process as defined in claim 1, wherein said ion exchange resin is a lead-carrying ion exchange resin containing an acid group.

8. The process as defined in claim 7, wherein said acid group is an aminophosphate group.

9. The process as defined in claim 1, wherein said catalyst contains a carboxyl group.

10. The process as defined in claim 1, wherein a concentration of said unsaturated aldehyde in said aqueous solution is in a range between 5 percent by weight and 50 percent by weight.

11. The process as defined in claim 1, wherein a concentration of said unsaturated aldehyde in said aqueous solution is in a range between 17 percent by weight and 50 percent by weight.

12. The process as defined in claim 1, wherein a concentration of said unsaturated aldehyde in said aqueous solution is in a range between 20 percent by weight and 50 percent by weight.